United States Patent
Alves et al.

(10) Patent No.: US 12,105,177 B2
(45) Date of Patent: Oct. 1, 2024

(54) ASSESSMENT OF POSITION OF MOTION TRACKERS ON A SUBJECT BASED ON WIRELESS COMMUNICATIONS

(71) Applicant: SWORD Health S.A., Oporto (PT)

(72) Inventors: José Carlos Coelho Alves, Oporto (PT); Márcio Filipe Moutinho Colunas, Oporto (PT); Luís António Correia de Oliveira, Oporto (PT); Pedro Filipe Xavier Rodrigues, Oporto (PT); Pedro Miguel Simões Bastos Martins, Oporto (PT); Pedro Miguel Moreira de Sousa, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 17/366,664

(22) Filed: Jul. 2, 2021

(65) Prior Publication Data
US 2023/0003863 A1    Jan. 5, 2023

(30) Foreign Application Priority Data

Jul. 1, 2021  (EP) .................................. 21398009

(51) Int. Cl.
*G01S 11/04*     (2006.01)
*G01P 15/00*     (2006.01)

(52) U.S. Cl.
CPC .............. *G01S 11/04* (2013.01); *G01P 15/00* (2013.01)

(58) Field of Classification Search
CPC .................................. G01S 11/04; G01P 15/00
See application file for complete search history.

(56) References Cited

U.S. PATENT DOCUMENTS

| 10,962,655 B2 * | 3/2021 | Pan .................... G01S 19/45 |
| 2005/0105600 A1 * | 5/2005 | Culum .................... G01S 5/04 |
| | | 375/150 |

(Continued)

FOREIGN PATENT DOCUMENTS

| EP | 3792928 A1 | 3/2021 |
| EP | 4117317 A1 | 1/2023 |

(Continued)

OTHER PUBLICATIONS

EP Application No. 21398009.7 Extended European Search Report dated Dec. 12, 2022.

*Primary Examiner* — Alexander Satanovsky
*Assistant Examiner* — Sangkyung Lee
(74) *Attorney, Agent, or Firm* — SCHWEGMAN LUNDBERG & WOESSNER, P.A.

(57) ABSTRACT

Motion tracking systems and methods for determining how a plurality of trackers is positioned on a plurality of body members of a person may include: wirelessly receiving, by a computing device, one or more first data packets of each tracker of the plurality of trackers; digitally determining a first direction in which the computing device is relative to the respective tracker by computing an angle of departure of the one or more first data packets; digitally determining based on the first directions, a second direction in which each tracker of the plurality of trackers is relative to one or more other trackers of the plurality of trackers; and digitally determining on which body member is each tracker of the plurality of trackers positioned on the person at least based on both the second directions and the plurality of body members requiring to have a tracker positioned thereon.

20 Claims, 4 Drawing Sheets

(56) References Cited

U.S. PATENT DOCUMENTS

| | | | |
|---|---|---|---|
| 2005/0215888 A1* | 9/2005 | Grimm | A61B 90/39 |
| | | | 606/130 |
| 2008/0262772 A1* | 10/2008 | Luinge | A61B 5/4528 |
| | | | 702/94 |
| 2011/0275957 A1* | 11/2011 | Bhandari | A61B 5/1114 |
| | | | 600/595 |
| 2012/0280902 A1* | 11/2012 | Persaud | A63F 13/211 |
| | | | 345/156 |
| 2018/0150131 A1 | 5/2018 | Ranieri et al. | |
| 2018/0160394 A1* | 6/2018 | Reunamäki | H04L 69/22 |
| 2019/0212359 A1 | 7/2019 | Erivantcev et al. | |
| 2020/0264256 A1* | 8/2020 | Stitt | G01S 3/04 |

FOREIGN PATENT DOCUMENTS

| | | | | |
|---|---|---|---|---|
| WO | WO-2019239365 A1 | | 12/2019 | |
| WO | WO-2019243438 A1 | * | 12/2019 | G06F 3/0346 |

* cited by examiner

ASSESSMENT OF POSITION OF MOTION TRACKERS ON A SUBJECT BASED ON WIRELESS COMMUNICATIONS

CROSS-REFERENCE TO RELATED APPLICATIONS

This application is related to and claims the benefit of European Patent Application No. 21398009, filed on Jul. 1, 2021, and titled, "Assessment of Position of Motion Trackers on a Subject Based on Wireless Communications", the contents of which are herein incorporated by reference in their entirety.

TECHNICAL FIELD

The present disclosure relates to the technical field of motion tracking systems. More particularly, it relates to assessment of the placement of motion trackers on a subject like e.g. a person so that accurate motion tracking sequence of the subject, e.g. person or body members thereof can be provided.

BACKGROUND

Many motion tracking systems have motion trackers, also referred to herein as trackers or inertial measurement units (IMUs), that are arranged on the target whose motion is to be tracked. The trackers include inertial sensors that measure e.g. orientations, angular velocities, accelerations, forces, etc., which may then be used to derive the motion of the tracked target.

One of the problems of motion tracking systems relying on motion trackers is that the motion tracking sequence provided is influenced by the positioning of the trackers. The computing device in charge of providing the motion tracking sequence considers that each particular tracker is arranged on a certain position on the tracked target, and the measurements from the respective inertial sensors represent how said certain position has moved over time. Non-correspondence between the position considered by the computing device and the actual position of the tracker, namely, wrongly positioned trackers, results in the provision of a motion tracking sequence that is not accurate.

Inaccurate motion tracking sequences are particularly problematic when the person conducts a physical rehabilitation procedure using a motion tracking system. The person does not require the supervision of a doctor or therapist thanks to the motion tracking system, which digitally and automatically supervises the rehabilitation procedure. In rehabilitation procedures, the person has to exercise by moving body members in a certain way to recover the mobility of an injured part of the body or reduce the pain that the person suffers, for example by performing stretching movements. With these procedures, the user can recover from a hip injury, a shoulder injury, a neck injury, etc. more rapidly. When the movements are incorrectly supervised, the person that rehabilitates runs the risk of getting injured even if she/he knows which movements she/he must perform because the person does not know whether all the movements and repetitions thereof are correctly reproduced.

The process of knowing which motion tracker is placed in each member is usually performed by a step of calibration. The person is asked to perform certain movements that will allow the computing device to infer in which part of the body each motion tracker is placed. However, this process is still vulnerable to possible user mistakes while performing the movements, for instance, moving the wrong member (the left instead of the right). This kind of mistake impacts the execution of the exercises since the computing device will be assuming that the motion trackers are in the wrong positions. By way of example, movements of the right or left leg will be considered as each other when the person moves the wrong side while performing calibration of the motion tracking system.

Accordingly, there is a need for an automatic assessment involving determination of on which body member each motion tracker is placed.

SUMMARY

A first aspect of the disclosure relates to a method for determining how a plurality of trackers is positioned on a plurality of body members of a person, a motion tracking system comprising the plurality of trackers, and a computing device, each tracker of the plurality of trackers being adapted to be arranged on a body of the person and comprising at least one inertial sensor and a plurality of antennas, the computing device comprising at least one antenna, the method comprising:

wirelessly receiving, by each tracker of the plurality of trackers from the computing device, one or more first data packets through each antenna of the plurality of antennas of the respective tracker at least while the tracker is positioned on the body of the person;

digitally determining, by each tracker of the plurality of trackers, a first direction in which the computing device is relative to the respective tracker by computing an angle of arrival of the one or more first data packets based on the reception thereof through each antenna of the respective plurality of antennas;

wirelessly receiving, by the computing device from each tracker of the plurality of trackers, one or more second data packets comprising data indicative of or relative to the respective first direction;

digitally determining, by the computing device, based on the received data from each tracker of the plurality of trackers, a second direction in which each tracker of the plurality of trackers is relative to one or more other trackers of the plurality of trackers; and digitally determining, by the computing device, on which body member is each tracker of the plurality of trackers positioned on the person at least based on both the second directions and the plurality of body members requiring to have a tracker positioned thereon, thereby providing a correspondence between the plurality of trackers and the plurality of body members.

The computing device relies on the reception of the first directions from the trackers to assess how the different trackers are positioned on the person. In this sense, the trackers establish the first directions by way of the multiple antennas thereof.

Each antenna receives the electromagnetic waves corresponding to the first data packets transmitted by the computing device and each tracker processes the waves respectively received so as to compute the angle of arrival accordingly. The computation of the angles of arrival is, for example, based on phase differences between the receptions of all the antennas of the plurality of antennas as known in the art, and/or differences in time of arrival of the receptions of all the antennas of the plurality of antennas as known in the art.

The first data packets may be any transmitted by the computing device, for example: advertisement packets, hand-shaking packets, data packets whereby the computing device requests angle of arrival computation and transmission of first directions by the trackers, etc.

The computed first directions, which may be e.g. the raw angles of arrival, processed angles of arrival (e.g. inverse angles), linear or polar or spherical coordinates or a subset thereof (i.e. one of the coordinates not defined), etc., are transmitted by the trackers to the computing device for processing by the latter. The processing by the computing device provides data indicative of where roughly each tracker is relative to the other trackers. Such data can be in the form of quadrants, angles, coordinates, etc. With this data, the computing device derives on which body member each tracker is owing to the information of which body members shall have a tracker positioned thereon. This means that the computing device has data indicating the body members that shall have a tracker, which will vary depending on the exercise to be performed by the user (in the context of the present disclosure the terms user and person are used interchangeably) and/or the body members whose motion is to be tracked, and data indicating how each body member is positioned relative to the other body members (with e.g. quadrants, angles, coordinates, etc.); the latter data may also be set for a given posture, preferably a straight posture. By way of example, the computing device has data indicating that the two shanks and the two thighs shall have a tracker arranged thereon, and data indicating that both each thigh is above each respective shank and that the right thigh and shank are to the right of the left thigh and shank.

With the two sets of data and the second directions, the computing device provides the correspondence to be used in the motion tracking procedure so that the computing device registers or reproduces the measurements of the trackers on the corresponding virtual body members.

The correspondence is defined by the computing device so as to minimize differences between the second directions and the body members relative to other body members. In this sense, the computing device may rely on differences between the position of one tracker and the position(s) of other tracker(s), and the differences between the positions of one body member and the position(s) of other body member(s). When the differences in the position of trackers is provided, for example, as angles or components thereof (e.g. horizontal, vertical and/or transversal components), these are compared with analogous values of body members to find the correspondence that minimizes a sum of differences between tracker positions and body member positions. In order to simplify the computations that have to be performed by the computing device, ranges in the position of one body member relative to other body members may be provided (e.g. the head of a person has an angular variation in the horizontal component of 0° to 10° in absolute value relative to the chest because they are substantially contained within a plane parallel to the coronal plane, whilst an angular variation in the horizontal component is, in absolute value, between 80° to 100° because it is above).

A second aspect of the present disclosure relates to a method for determining how a plurality of trackers is positioned on a plurality of body members of a person, a motion tracking system comprising the plurality of trackers, and a computing device, each tracker of the plurality of trackers being adapted to be arranged on a body of the person and comprising at least one inertial sensor and a plurality of antennas, the computing device comprising at least one antenna, the method comprising:

wirelessly receiving, by the computing device from each antenna of the plurality of antennas, one or more first data packets of each tracker of the plurality of trackers at least while the respective tracker is positioned on the body of the person;

digitally determining, by the computing device, a first direction in which the computing device is relative to the respective tracker by computing an angle of departure of the one or more first data packets based on the reception thereof through each antenna of the respective plurality of antennas of the respective tracker, the computing device comprising data indicative of a distance that each pair of antennas of the plurality of antennas is apart for each respective tracker;

digitally determining, by the computing device, based on the first directions, a second direction in which each tracker of the plurality of trackers is relative to one or more other trackers of the plurality of trackers; and digitally determining, by the computing device, on which body member is each tracker of the plurality of trackers positioned on the person at least based on both the second directions and the plurality of body members requiring to have a tracker positioned thereon, thereby providing a correspondence between the plurality of trackers and the plurality of body members.

The computing device relies on the reception of the first data packets from several or all the antennas of each tracker to assess how the different trackers are positioned on the person.

The computing device receives the electromagnetic waves corresponding to the first data packets transmitted by different antennas of the trackers and processes them so as to compute the angle of departure accordingly. The computation of the angles of departure is, for example, based on phase differences between the receptions of same packets transmitted by different antennas as known in the art, and/or differences in time of arrival of the receptions of same packets transmitted by different antennas as known in the art.

The first data packets may be any transmitted by the trackers, for example: advertisement packets, hand-shaking packets, data packets with measurements of the at least one inertial sensor of each respective tracker, etc. The second data packets may be any transmitted by the trackers, for example: advertisement packets, hand-shaking packets, data packets with measurements of the at least one inertial sensor of each respective tracker, etc.

The processing of the first directions provides data indicative of where roughly each tracker is relative to the other trackers. Such data can be in the form of quadrants, angles, coordinates, etc. Like in the first aspect of the disclosure, with the two sets of data and the second directions, the computing device provides the correspondence to be used in the motion tracking procedure so that the computing device registers or reproduces the measurements of the trackers on the corresponding virtual body members.

A third aspect of the present disclosure relates to a method for determining how a plurality of trackers is positioned on a plurality of body members of a person, a motion tracking system comprising the plurality of trackers, and a computing device, each tracker of the plurality of trackers being adapted to be arranged on a body of the person and comprising at least one inertial sensor and at least one antenna, the computing device comprising a plurality of antennas, the method comprising:

wirelessly receiving, by the computing device from each tracker of the plurality of trackers, one or more first data packets through each antenna of the plurality of antennas at least while the respective tracker is positioned on the body of the person;

digitally determining, by the computing device, a first direction in which the computing device is relative to each tracker of the plurality of trackers by computing an angle of arrival of the one or more first data packets based on the reception thereof through each antenna of the plurality of antennas;

digitally determining, by the computing device, based on the first directions, a second direction in which each tracker of the plurality of trackers is relative to one or more other trackers of the plurality of trackers; and digitally determining, by the computing device, on which body member is each tracker of the plurality of trackers positioned on the person at least based on both the second directions and the plurality of body members requiring to have a tracker positioned thereon, thereby providing a correspondence between the plurality of trackers and the plurality of body members.

The computing device relies on the reception of the first data packets through each antenna thereof to assess how the different trackers are positioned on the person.

The computing device receives the electromagnetic waves corresponding to the first data packets transmitted by each tracker and processes them so as to compute the angle of arrival thereof accordingly. The computation of the angles of arrival is, for example, based on phase differences between the receptions of same packets transmitted by different antennas as known in the art, and/or differences in time of arrival of the receptions of same packets transmitted by different antennas as known in the art.

The first data packets may be any transmitted by the trackers, for example: advertisement packets, hand-shaking packets, data packets with measurements of the at least one inertial sensor of each respective tracker, etc.

The processing of the first directions provides data indicative of where roughly each tracker is relative to the other trackers. Such data can be in the form of quadrants, angles, coordinates, etc. Like in the first and second aspects of the disclosure, with the two sets of data and the second directions, the computing device provides the correspondence to be used in the motion tracking procedure so that the computing device registers or reproduces the measurements of the trackers on the corresponding virtual body members.

In some embodiments of each of the first, second and third aspects, in the step of digitally determining on which body member is each tracker positioned the digital determination is based on both the second directions and a predetermined correspondence between the plurality of trackers and the plurality of body members, and said step further comprises at least one of:

digitally modifying the predetermined correspondence when the computing device digitally determines that the body member that at least one tracker of the plurality of trackers is on does not correspond to a respective tracker position in the predetermined correspondence, and the predetermined configuration of tracker positions is digitally modified such that the correspondence between the plurality of trackers and the body members corresponds with the second directions; and commanding provision of one or more user perceptible signals indicative of at least one of: incorrect positioning of at least one tracker of the plurality of trackers, and guidance on how to reposition at least one incorrectly positioned tracker.

The process for assessing the position of the motion trackers can follow a calibration process whereby the person positions the motion trackers according to the predetermined correspondence (e.g. tracker number one goes to the right upper arm, tracker number two goes the chest, etc.) that the computing device may command to provide to the person by way of user perceptible signals.

In such scenarios, people nevertheless inadvertently swap motion trackers and position them without fulfilling the predetermined correspondence. The process for assessing the position of the motion trackers detects the incorrect positioning (i.e. a positioning of motion trackers that does not fulfill the predetermined correspondence) and either digitally modifies it or informs the person for repositioning the motion trackers.

In some embodiments of each of the first, second and third aspects, the step of digitally determining on which body member is each tracker positioned comprises commanding the provision of the one or more user perceptible signals, and the method further comprises repeating the steps leading to the digital digitally determination of on which body member is each tracker of the plurality of trackers positioned on the person in order to assess whether the person has repositioned the one or more trackers according to the predetermined configuration of tracker positions.

When following the calibration process it is determined that motion trackers do not fulfill the predetermined correspondence and the person is informed about that situation to prompt the person to reposition the motion trackers, the process for assessing the positions of the motion trackers is repeated, thereby reassessing the positions in case the person has once again misplaced some trackers.

In some embodiments of each of the first, second and third aspects, the plurality of antennas (of the trackers or the computing device) comprises at least three antennas arranged such that there is no imaginary line that can be drawn containing all of the at least three antennas. In this sense, in some embodiments, at least one of the plurality of antennas is arranged staggered relative to other antennas of the plurality of antennas along a first axis of the device (tracker or computing device), and at least one of the plurality of antennas is arranged staggered relative to other antennas of the plurality of antennas along a second axis of the device (tracker or computing device).

The antennas arranged in such a way that they are not aligned (i.e. no imaginary line contains them all) may produce greater differences between the captured electromagnetic waves and, thus, received data packets. This, in turn, results in better precision in establishing both the angles of arrival and departure, and the first directions, and especially when, in some embodiments, the first and second directions each at least include two perpendicular components thereby being at least indicative of two-dimensional directions. This means that each angle of arrival or departure that is computed comprises first and second angles relative to two perpendicular components. Hence, the second directions at least include horizontal and vertical components.

The staggered arrangement makes the plurality of antennas to at least form a two-dimensional array that enhances the computing of the angle of arrival and departure in at least two different axes.

In some embodiments of each of the first, second and third aspects, during the step of wirelessly receiving the data packets based on which the first directions are digitally determined the person is positioned such that a normal vector of a coronal plane of the person forms an angle with a line intersecting both the computing device and a belly button of the person whose absolute value is less than or equal to 45°.

The second directions determined by the computing device are more accurate when said absolute value of the angle is between 0° and 45°. For angles above 45°, the components and/or the first directions themselves are less different from others because part of trackers may be on the projection of other trackers (relative to the computing device). The accuracy in determining on which body member is each tracker of the plurality of trackers positioned on the person becomes lower when the absolute value of the angle exceeds 45°, and particularly the closer the angle gets to 90°, mostly due to the joints of the person being contained in the coronal plane or in a plane parallel thereto.

In some embodiments of each of the first, second and third aspects, during the step of wirelessly receiving the data packets based on which the first directions are digitally determined the person is in a straight posture.

Owing to both the orientations and the separation of the body members, the straight posture typically results in a greater accuracy in determining on which body member is each tracker of the plurality of trackers positioned on the person.

In some embodiments of each of the first, second and third aspects, the method further comprises digitally estimating, by the computing device, a distance that the computing device is apart from each tracker of the plurality of trackers based on the data packets wirelessly received from each tracker of the plurality of trackers; and each second direction at least includes three perpendicular components thereby being indicative of a three-dimensional direction.

With the distances to the trackers, and together with the angle of arrival or departure, the computing device is capable of deriving a 3D direction for each tracker. With 3D directions the computing device is also capable of determining the position of trackers on body members when two trackers are, relative to the computing device, partially or completely superposed, namely one is partially or completely in the projection of the other. In this way, by way of example, the computing device may establish which motion tracker is on the back of the person and which motion tracker is on the chest of the person. By way of another example, the computing device may establish which motion tracker is on the left upper arm of the person and which motion tracker is on the right upper arm of the person while the person is standing with an angle between a normal vector of the coronal plane and a line intersecting both the computing device and the belly button of the person having an absolute value above 45° or even sideways, i.e. the person is not facing the computing device but is rather facing in a direction perpendicular to a direction of the line, namely 90°.

In some embodiments of each of the first, second and third aspects, the step of digitally determining on which body member is each tracker of the plurality of trackers positioned on the person further comprises determining a position of each tracker on a surface of the respective body member on which the tracker is.

The computing device may compute the 3D positions of the different trackers, thereby making possible to determine where on the surface of the body members each tracker is.

The knowledge of the position on the body member is also important for a more accurate motion tracking procedure because the movements and accelerations of the motion trackers are not the same when positioned e.g. closer to one joint than another, on the side of the body member than on the front, etc.

So, the computing device in some embodiments improves the motion tracking procedure by digitally assigning the positions of the trackers to those determined, in which case the registering and/or reproduction of the measurements of the trackers will be more accurate, and in some other embodiments requests the person to reposition one or some of the trackers if the positions thereof is considered to be inadequate. To this end, the computing device has data indicative of correct positions or correct areas where the trackers can be positioned on each body member, and the device compares the computes positions with this data to determine whether the positions are inadequate.

In some embodiments of each of the first, second and third aspects, the computing device digitally estimates the distances by at least one of:

digitally processing a received signal strength indicator, i.e. RSSI, included in the data packets wirelessly received from each tracker of the plurality of trackers; and digitally processing a level of power with which the computing device captures electromagnetic waves of data packets wirelessly received from each tracker of the plurality of trackers.

The computing device receives RSSI in the data packets it receives from the trackers, and/or regards the level of power of captured electromagnetic waves as an indication of distance, the distance being greater when the level of power is smaller. Regarding the former, each tracker preferably computes an RSSI when it receives data packets from the computing device, and said RSSI may then be transmitted to the computing device.

In some embodiments of each of the first and third aspects, the data packets are wirelessly received using a wireless communications protocol comprising computation of angle of arrival of data packets wirelessly received. For example, but without limitation, Bluetooth version 5.1 or greater.

In some embodiments of the second aspect, wherein the data packets are wirelessly received using a wireless communications protocol comprising computation of angle of departure of data packets wirelessly received. For example, but without limitation, Bluetooth version 5.1 or greater.

A fourth aspect of the disclosure relates to a motion tracking system comprising: a plurality of trackers adapted to be arranged on a body of a person, and comprising: at least one inertial sensor, and a plurality of antennas; and a computing device comprising at least one antenna, the computing device being adapted to execute steps of a method according to first and/or second aspects of the disclosure and/or embodiments thereof. The computing device may be adapted in that manner by way of at least one processor and at least one memory configured to execute such steps; a computer program having instructions to that end may be stored in at least one memory.

A fifth aspect of the disclosure relates to a motion tracking system comprising: a plurality of trackers adapted to be arranged on a body of a person, and comprising: at least one inertial sensor, and at least one antenna; and a computing device comprising a plurality of antennas, the computing device being adapted to execute steps of a method according to the third of the disclosure and/or embodiments thereof. The computing device may be adapted in that manner by way of at least one processor and at least one memory configured to execute such steps; a computer program having instructions to that end may be stored in at least one memory.

In some embodiments of each of the fourth and fifth aspects, the motion tracking system and/or the computing device comprises one or more devices adapted to provide user perceptible signals, for example, one or more of: a screen, loudspeakers, vibrating devices, light emitters, etc.

A sixth aspect of the disclosure relates to a data processing apparatus comprising at least one processor adapted to perform a method, or steps of a method conducted by the computing device, according to the first, second and/or third aspects of the disclosure and/or embodiments thereof.

A seventh aspect of the disclosure relates to a computer program product that has instructions which, when executed by a computing device, cause the computing device to perform a method, or steps of a method conducted by the computing device, according to the first, second and/or third aspects of the disclosure and/or embodiments thereof.

Upon running the computer program product on one or more processors of the computing device, the computing device assesses the placement of the one or more trackers on the body of the person.

In some embodiments, the computer program product is embodied on a non-transitory computer-readable medium or a computer-readable data carrier has the computer program product stored thereon.

An eighth aspect of the disclosure relates to a data carrier signal carrying a computer program product according to the seventh aspect of the disclosure.

Similar advantages as those described for the first, second and third aspects of the disclosure are also applicable to the fourth, fifth, sixth, seventh and/or eighth aspects of the disclosure.

BRIEF DESCRIPTION OF THE DRAWINGS

To complete the description and in order to provide for a better understanding of the disclosure, a set of drawings is provided. Said drawings form an integral part of the description and illustrate embodiments of the disclosure, which should not be interpreted as restricting the scope of the disclosure, but just as examples of how the disclosure can be carried out. The drawings comprise the following figures.

DETAILED DESCRIPTION OF THE DRAWINGS

Figure 1:
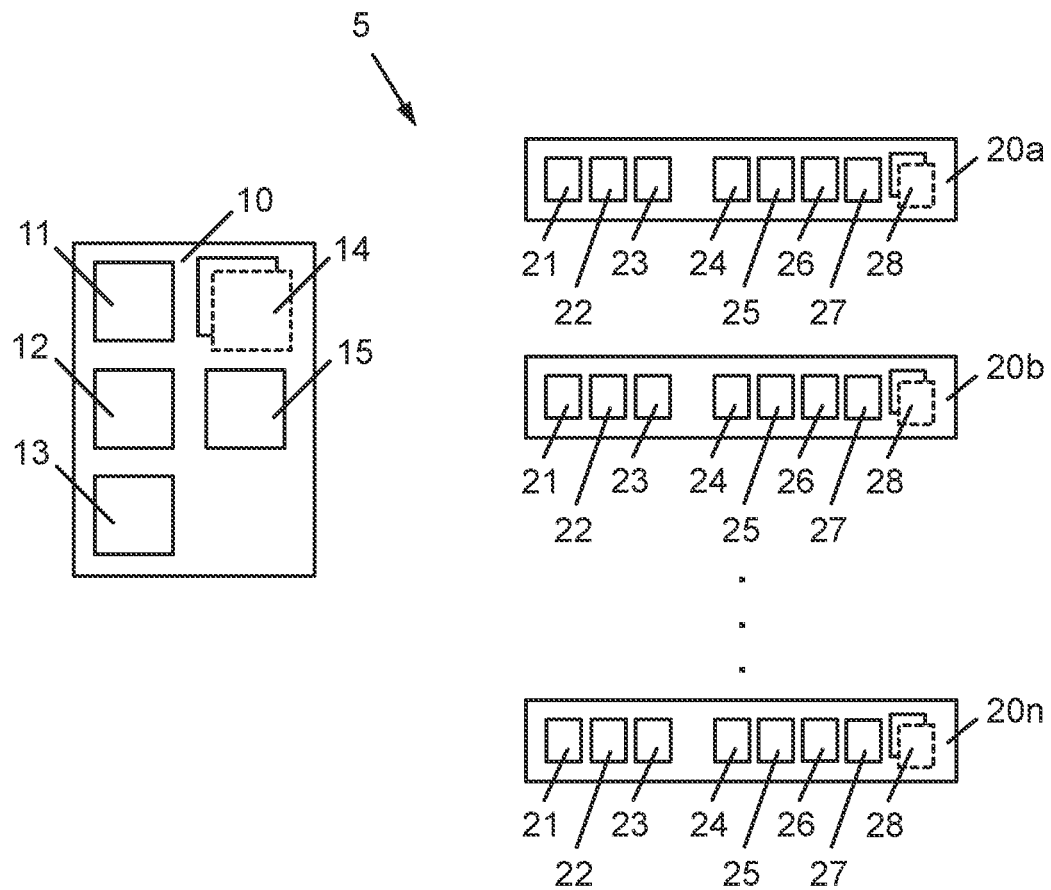
FIG. 1 diagrammatically shows a motion tracking system in accordance with embodiments.

FIG. 1 diagrammatically shows a motion tracking system 5 in accordance with embodiments. The motion tracking system 5 includes a computing device 10, which may be e.g. a tablet, a mobile phone, a personal computer, etc., and one or more trackers 20a-20n, i.e. inertial measurement units.

Each tracker 20a-20n includes one or more inertial sensors selected from e.g. an accelerometer 21, a gyroscope 22 and a magnetometer 23. In the embodiment of FIG. 1, each tracker 20a-20n includes all three inertial sensors 21-23, but in other embodiments the trackers only include an accelerometer 21 and a gyroscope 22, for instance. Preferably, all IMUs 20a-20n include the same inertial sensors 21-23.

The trackers 20a-20n further include at least one processor 24, at least one memory 25, and a first wireless communications module 26 for transmitting radiofrequency signals to and receiving radiofrequency signals from the computing device 10. For example, the trackers 20a-20n transmit advertisement packages, data packets with identification data (e.g. one or more identities, keys, etc.), data packets with measurements of the inertial sensor(s) 21-23, data packets with directions computed by the trackers, combinations thereof, etc., and receive packets from the computing device 10 with e.g. instructions to compute an angle of arrival of incoming communications, identification data, etc. At least when no wireless communications connections are established with the computing device 10, the radiofrequency signals of the trackers 20a-20n include advertisement packages for indicating their presence and that they are active. Once the wireless communications connections are established (using a technology and protocol known by a skilled person, for instance but without limitation, Bluetooth and Bluetooth Low Energy communications, cellular network communications such as GSM, UMTS or LTE, wireless LAN communications, etc.) with the computing device 10, the radiofrequency signals of the trackers 20a-20n may include identification data, directions, and/or the measurements, based on which the motion tracking sequence will be provided by the computing device 10.

In some aspects and in some embodiments, each tracker 20a-20n comprises a plurality of antennas 28 for radiating and capturing electromagnetic waves as part of the operation of the first wireless communications module 26. In some other aspects and in some other embodiments, each tracker 20a-20n comprises one antenna 28.

Each tracker 20a-20n is adapted to be arranged on the body of a person so that the measurements provided by each tracker 20a-20n can be processed by the computing device 10, thereby providing a motion tracking sequence of the person. The trackers 20a-20n may be attached to body members of the person by means of an attaching device 27 like, for instance, straps, Velcro, etc., that the motion tracking system 5 or the tracker 20a-20n itself comprises.

Preferably, at least one processor 24 of the trackers 20a-20n runs a sensor fusion algorithm for processing the measurements of the inertial sensors 21-23 within the respective tracker. The sensor fusion algorithm is intended to enhance the raw measurements of the inertial sensors by correcting errors thereof due to drifts of the inertial sensors and, thus, outputs processed measurements that are to be transmitted to the computing device 10.

The computing device 10 includes at least one processor 11, at least one memory 12, and a second wireless communications module 13 for transmitting radiofrequency signals to the trackers 20a-20n and receive radiofrequency signals therefrom. In some aspects and in some embodiments, the computing device 10 includes a plurality of antennas 14, whereas in some other aspects and in some other embodiments, the computing device 10 includes one antenna 14. The antenna(s) 14 cooperate with the second wireless communications module 13.

In all aspects and embodiments, at least one among the trackers 20a-20n and the computing device 10 comprise a plurality of antennas 14, 28. In some embodiments, both the trackers and the computing device 10 comprise a plurality of antennas 14, 28.

The motion tracking system 5 also includes at least one device 15 (which can be part of the computing device 10 or be separate from the computing device 10) for providing user perceptible signals like e.g. a screen or loudspeakers, to name a few examples. That is to say, the at least one device 15 comprises one or more of visual output means (e.g. screen, LEDs), audio output means (e.g. loudspeakers), vibrating means (e.g. a vibrator), etc. for providing user perceptible signals in the form of sounds, vibration, animated graphics, etc.

When the at least one device 15 comprises a screen, the computing device 10 is capable of showing instructions and/or information to the intended user about the operation of the motion tracking system 5 and the motion tracking procedure to be conducted with the system 5, for example predetermined movements that are to be performed by an intended user of the motion tracking system 5, a list or representation of the body members that shall have a tracker arranged thereon for a given exercise or motion tracking procedure, results of the exercises performed by the user, etc. To this end, the computing device 10 stores, in the at least one memory 12, the predetermined body members where the trackers must be positioned, and also data relative to the physical exercises, i.e. predetermined movements, of intended users. Any of these data can be transmitted to and/or received from another electronic device thanks to the second wireless communications module 13. For example, a therapist is able to receive the feedback at a computing device in a hospital so as to monitor the evolution of the person. Based on the feedback received, the therapist is able to adjust the difficulty of the movement(s), the number of repetitions thereof, prescribe new movements, etc. so that the person may further exercise using the motion tracking system 5.

Figure 2A:
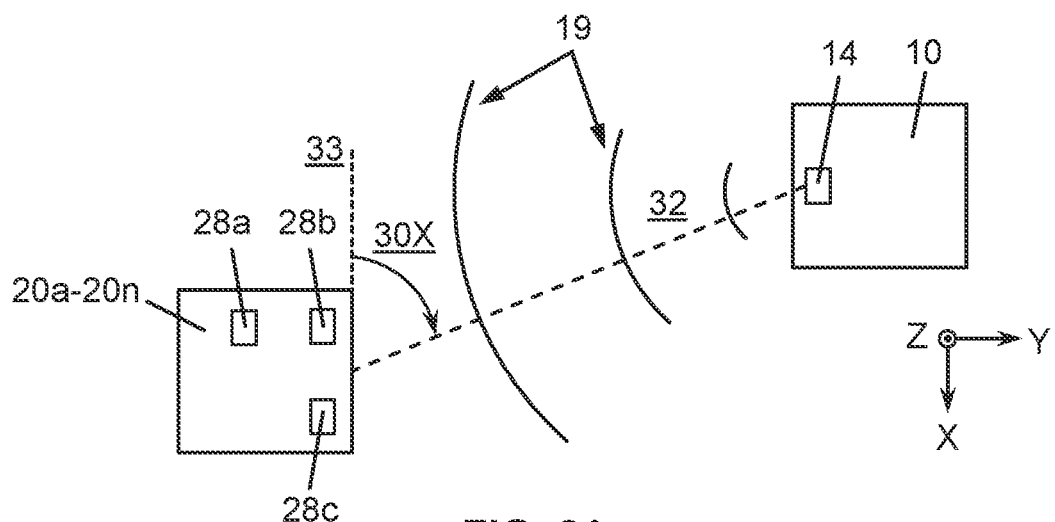
FIGS. 2A, 2B and 3A, 3B diagrammatically show exemplary angle of arrival and angle of departure computations in motion tracking systems in accordance with embodiments.
Figure 2B:
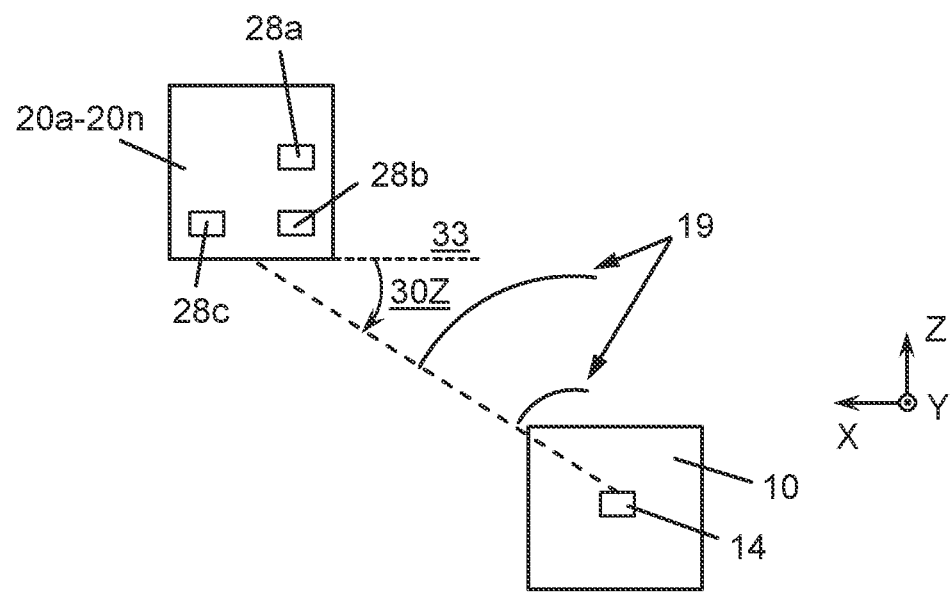

FIGS. 2A and 2B diagrammatically show an exemplary angle of arrival 30 computation in motion tracking systems in accordance with embodiments from two different views. For the sake of clarity only, one tracker 20a-20n has been represented although a motion tracking system according to the present disclosure comprises a multiplicity of trackers 20a-20n.

In this example, the computing device 10 of a motion tracking system comprises at least one antenna 14 (in this example one antenna whereas, in some embodiments, it is two antennas, three antennas or even more antennas), and the trackers 20a-20n of the system each comprises a plurality of antennas 28a-28c (in this example three antennas whereas, in some embodiments, it is two antennas, four antennas or even more antennas) that, moreover, is arranged so as to form a two-dimensional array. This, in turn, allows more accurate computation of angle of arrival in the vertical direction (i.e. the Z axis direction).

The computing device 10 transmits data packets by way of electromagnetic waves 19 (shown as arcs for the sake of simplicity only, it will be noted that the radiation by the antennas is typically omnidirectional) radiated through at least one antenna 14. The electromagnetic waves 19 are captured by each of the antennas 28a-28c of each tracker 20a-20n, and each tracker 20a-20n computes, based on the waves 19 that the antennas 28a-28c it respectively comprises have captured, an angle of arrival 30. As it can be appreciated from the represented waves 19, a same wave arrives at each antenna 28a-28c with a different phase and time delay, which once processed together with the phase and/or time delay of the same wave as received by the different antennas 28a-28c provides the angle of arrival 30. For the computation of the angles of arrival 30, each tracker has data indicative of how the antennas are arranged in the tracker so as to process the differences in phase and/or time delay, which can include the relative positions of each antenna to the others, the position of the antennas on a printed circuit board of the tracker, the distances between the antennas, etc. Also, in some embodiments, data indicative of the orientation of the trackers is used in addition to the arrangement of the antennas for the computation of the angles of arrival 30, which makes possible to compute the angles more accurately; said data is preferably the measurements of one or more sensor device(s) of the tracker, e.g. measurements of the gyroscope and/or measurements of the accelerometer.

As shown in the two different views of FIGS. 2A and 2B that each is a 2D representation, the angle of arrival 30 is typically decomposed in two angles or values 30X, 30Z, one for a horizontal component 30X, in this case the horizontal component is with respect to an XY plane, and one for a vertical component 30Z, in this case the vertical component is with respect to an XZ plane. The angle of arrival 30 and the components thereof can be computed with respect to any axis predefined in the trackers, in this example the axis 33 (represented with a dashed line for illustrative purposes only) is parallel to the X axis.

With the angle of arrival 30X, 30Z computed, each tracker 20a-20n computes a first direction 32 (shown with a dashed line for illustrative purposes only) indicative of where the computing device 10 or the at least one antenna 14 thereof is relative to the respective tracker 20a-20n. In this example, the direction 32 is defined with respect to a middle point of a front face or edge of the illustrated tracker, but other point could be used instead, for example a corner, a center of the tracker, etc.

The trackers 20a-20n preferably compute angles of arrival 30 during a calibration time window, for instance at the beginning of the motion tracking session. The calibration time may have predetermined minimum and maximum times so as to delimit the time it takes to perform the assessment of the positions of the trackers.

Additionally, the angles of arrival 30 may be computed for the different packets received from the computing device 10 and then each tracker computes a respective mean angle of arrival by averaging the different angles of arrival 30, thereby reducing errors in angles of arrival due to sudden changes that may be caused, for instance, by interferences. In this sense, mean angles of arrival may be computed for each of the two components, namely the horizontal and vertical components of the angles of arrival. The averaging for the mean angles of arrival is carried out for packets received during the calibration time, and can be of as many packets as received during said calibration time or in a time window within the calibration time, in which case it is preferably a sliding time window that slides within the calibration time; the duration of the time window may have predetermined minimum and maximum times as well and be defined in time (e.g. 1 second, 2 seconds, etc.) or as a percentage of the calibration time (e.g. 10% of the calibration time, 15%, etc.).

In embodiments like the one illustrated, the angle of arrival 30 is computed by each tracker 20a-20n and is subsequently transmitted to the computing device 10, either as the angle of arrival 30, as the first direction 32, or an analogous value or parameter.

In other embodiments, the computing device 10 comprises a plurality of antennas and upon reception of electromagnetic waves radiated by each tracker (which may comprise one antenna or a plurality of antennas), the device 10 processes the phase and/or time delay thereof in the same manner described and computes the angle of arrival 30 and the first directions 32 for each tracker 20a-20n. For the computation, the computing device 10 has data indicative of how the antennas are arranged therein (e.g. relative positions of antennas, positions on a printed circuit board of the computing device, the distances between the antennas, etc.) so as to process the differences in phase and/or time delay. Also, in some embodiments, the computing device uses data indicative of the orientation of the trackers (in addition to the arrangement of the antennas) for the computation of the angles of arrival 30, which makes possible to compute the angles more accurately; said data is preferably the measurements of one or more sensor device(s) of the tracker, which are transmitted in packets to the computing device 10 (for instance, said packets are used by the computing device 10 to compute the angles of arrival 30).

Further, in addition to the angles of arrival 30 and the first directions 32, distances between the computing device 10 and each tracker 20a-20n can also be computed for enhanced position assessment of the trackers. The trackers 20a-20n can include the RSSI in the data packets where the first direction is sent to the computing device 10, or the computing device 10 may estimate the distance by processing the differences in RSSI or level of power between the wireless communications with each tracker 20a-20n, so an RSSI or level of power in the communications with a first tracker that is lower than an RSSI or level of power in the communications with a second tracker represents a greater distance for the first tracker. With reference to what is illustrated in FIGS. 2A and 2B, a distance between the computing device 10 and a tracker 20a-20n is a length of the first direction 32 illustrated.

The computing device 10 then uses the received data to compute second directions, i.e. the direction that each tracker 20a-20n is relative to the other trackers.

Figure 3A:
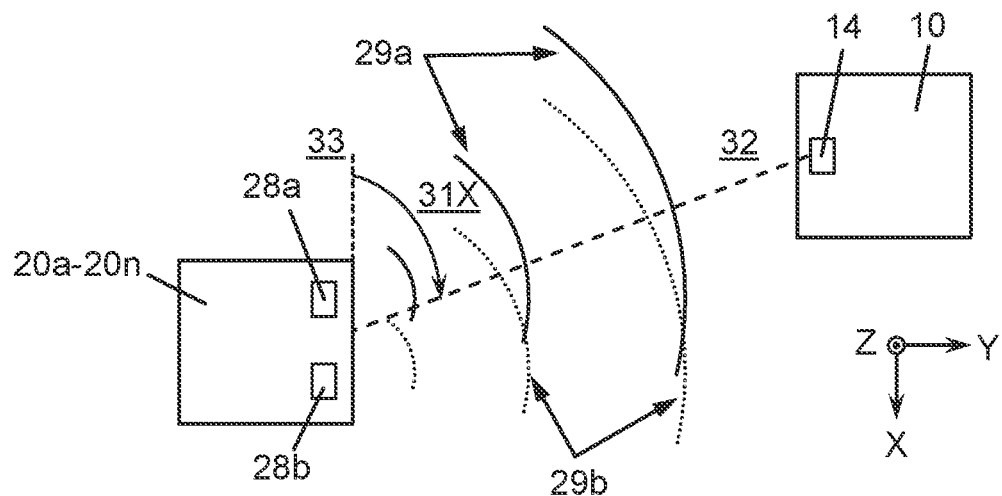
Figure 3B:
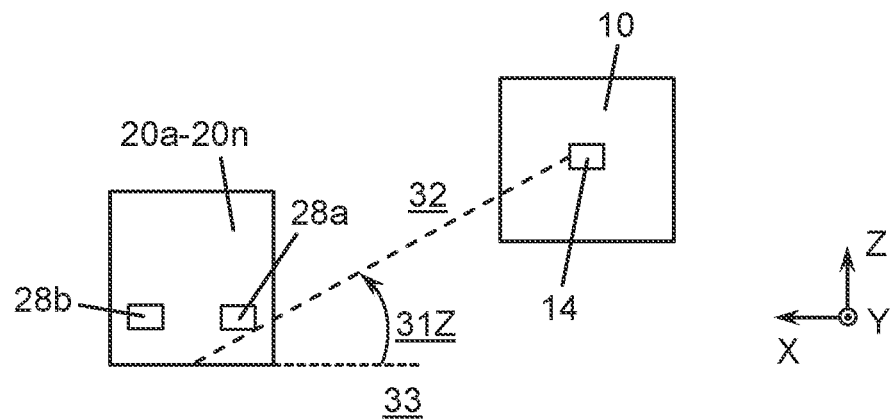

FIGS. 3A and 3B diagrammatically show an exemplary angle of departure 31 computation in motion tracking systems in accordance with embodiments from two different views. For the sake of clarity only, one tracker 20a-20n has been represented although a motion tracking system according to the present disclosure comprises a multiplicity of trackers 20a-20n.

In this example, the computing device 10 of a motion tracking system comprises at least one antenna 14 (in this example one antenna whereas, in some embodiments, it is two antennas, three antennas or even more antennas), and the trackers 20a-20n of the system each comprises a plurality of antennas 28a, 28b (in this example two antennas whereas, in some embodiments, it is three antennas, four antennas or even more antennas).

The trackers 20a-20n transmit data packets by way of electromagnetic waves 29a, 29b (shown as arcs for the sake of simplicity only, it will be noted that the radiation by the antennas is typically omnidirectional) radiated through each antenna 28a, 28b. The electromagnetic waves 29a, 29b are captured by the at least one antenna 14 of the computing device 10, and the device 10 computes, based on the waves 29a, 29b that the at least one antenna 14 has captured, an angle of departure 31. As it can be appreciated from the represented waves 29a, 29b, each antenna 28a, 28b radiates its own waves 29a, 29b of a same data packet, and each wave 29a arrives at the at least one antenna 14 with a different phase and time delay, which once processed together provides the angle of departure 31. For the computation of the angles of departure 31X, 31Z, the computing device 10 has data indicative of how the antennas of each tracker 20a-20n are arranged therein so as to process the differences in phase and/or time delay; to that end, the computing device 10 may have that the data already stored therein, for instance because the motion tracking system has predetermined trackers and the data about the antennas is already stored in a memory communicatively coupled with a processor of the computing device 10, or the trackers 20a-20n also transmit that data to the computing device 10. Likewise, in some embodiments, the computing device 10 uses data indicative of the orientation of the trackers 20a-20n (in addition to the arrangement of the antennas) for the computation of the angles of departure 31, which makes possible to compute the angles more accurately; said data is preferably the measurements of one or more sensor device(s) of the tracker 20a-20n, which are transmitted in packets to the computing device 10 (for instance, said packets are used by the computing device 10 to compute the angles of departure 31).

Like the angle of arrival 30 described in relation to FIGS. 2A and 2B, the angle of departure 31 is typically decomposed in two angles or values 31X, 31Z in the same manner described. And like the angle of arrival 30, the angle of departure 31 might be computed within a calibration time window and/or a mean angle of departure can be computed, including in decomposed form as horizontal and vertical components.

Further, in addition to the angles of departure 31 and the first directions 32, distances between the computing device 10 and each tracker 20a-20n can also be computed for enhanced position assessment of the trackers as described with reference to FIGS. 2A and 2B.

With the angle of departure 31 computed, the computing device 10 computes a first direction 32 (shown with a dashed line for illustrative purposes only) indicative of where each tracker 20a-20n is relative to the computing device 10 or the at least one antenna 14. Then the computing device 10 may further compute the second directions.

Figure 4:
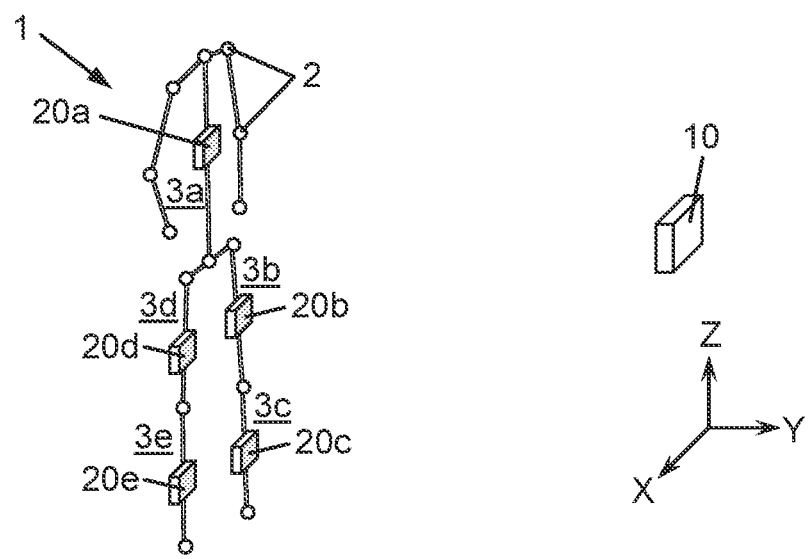
FIG. 4 shows a motion tracking system in accordance with embodiments while the trackers are positioned on a person.

FIG. 4 shows a motion tracking system in accordance with embodiments while the trackers are positioned on a person 1. For the sake of clarity only, the person 1 is shown as a simplified set of segments of body members 3a-3e and joints 2 that the body members 3a-3e are connected with.

The person 1 has a first tracker 20a positioned on a chest 3a, a second tracker 20b positioned on a left upper leg or thigh 3b, a third tracker 20c positioned on a left lower leg or shank 3c, a fourth tracker 20d positioned on a right upper leg or thigh 3d, and a fifth tracker 20e positioned on a right lower leg or shank 3e. It will be noted that other pluralities of trackers and other tracker positioning are possible within the scope of the present disclosure.

A computing device 10 intends to assess the position of each of the five trackers 20a-20e. To that end, the computing device 10 has data indicative of the body members that shall have a tracker arranged thereon for the motion tracking procedure or physical exercise that is or is to be carried out. This means that, in this example, the computing device 10 has data indicating that the chest 3a, left thigh 3b, left shank 3c, right thigh 3d and right shank 3e shall have a tracker positioned thereon.

Following a procedure as described with reference to FIGS. 2A, 2B, 3A and 3B whereby the computing device 10 computes the angles of departure or angles of arrival, or the trackers 20a-20e compute the angles of arrival, the computing device 10 establishes second directions of trackers as described with reference to FIG. 5.

Figure 5:
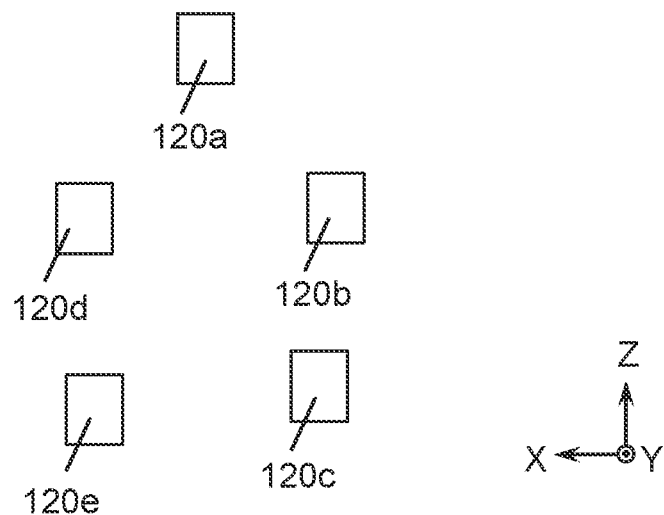
FIG. 5 diagrammatically shows a representation of how a computing device has established (second) directions of trackers with regards to the embodiment of FIG. 4.

In FIG. 5 is illustrated a representation of the tracker positions 120a-120e corresponding to the first to fifth trackers 20a-20e of FIG. 4 by a computing device 10. This representation is shown for the sake of clarity only.

The computing device 10 for example computes the second directions as delta angles of arrival or delta angles of departure, which are the differences in the angles of arrival between each pair of trackers or the differences in the angles of departure between each pair of trackers. These delta angles can likewise be computed or decomposed in the components of the angles of arrival or departure so that there is a horizontal delta angle of arrival component and a vertical delta angle of arrival component for one tracker with respect to another tracker.

By processing these second directions and a list of body members that shall have a tracker arranged thereon, the computing device 10 provides a correspondence between trackers and body members. In this case, the first tracker position 120a is higher along the Z axis than the rest tracker positions 120b-120e, and so is the chest with respect to the thighs and shanks. The second and fourth tracker positions 120b, 120d are at a lower height (with respect to the Z axis) but at a higher height than third and fifth tracker positions 120c, 120e, like thighs with respect to the chest and the shanks. The second tracker position 120b is to the left (when seen from the user's perspective, not from the computing device's perspective) of the fourth tracker position 120d, so the second tracker position 120b corresponds to the left thigh and the fourth tracker position 120d corresponds to the right thigh. A similar assessment is made regarding the remaining tracker positions.

For the sake of clarity only, Tables 1 to 4 are presented next to describe numerically with exemplary values the assignation just explained. These Tables in no way limit the scope of the present disclosure to the following types of values, tracker arrangements, body members, etc., and are only intended to illustrate how the assignation is carried out in some embodiments.

TABLE 1

Possible ranges of the absolute value of the difference between the first directions of each tracker placed on each specific body member. The values presented regard the ranges of angles of arrival (i.e. AoA) on the horizontal plane.

| Absolute value Rel AoA – X (horizontal plane) | Chest | Left Thigh | Right Thigh | Left Shank | Right Shank |
|---|---|---|---|---|---|
| Chest | — | 10-30° | 10-30° | 10-30° | 10-30° |
| Left Thigh | 10-30° | — | 30-60° | 0-5° | 30-60° |
| Right Thigh | 10-30° | 30-60° | — | 30-60° | 0-5° |
| Left Shank | 10-30° | 0-5° | 30-60° | — | 10-30° |
| Right Shank | 10-30° | 10-30° | 0-5° | 30-60° | — |

TABLE 2

The possible signal (positive or negative) of the difference between first directions of each tracker placed on each specific part of the body. The signals presented regard the angles of arrival on the horizontal plane. The angle is considered as positive to the right of the virtual 0 axis on the horizontal plane (parallel line to the coronal plane on the computing device – X axis on the FIG. 4).

| Signal value Rel AoA – X (horizontal plane) | Chest | Left Thigh | Right Thigh | Left Shank | Right Shank |
|---|---|---|---|---|---|
| Chest | — | – | + | – | + |
| Left Thigh | + | — | + | +– near 0 | + |
| Right Thigh | – | – | — | – | +– near 0 |
| Left Shank | + | +– near 0 | + | — | + |
| Right Shank | – | – | +– near 0 | – | — |

TABLE 3

Possible ranges of the absolute value of the difference between the first directions of each tracker placed on each specific body member. The values presented regard the ranges of angles of arrival on the vertical plane (parallel plane to the sagittal plane).

| Absolute value Rel AoA – Z (vertical plane) | Chest | Left Thigh | Right Thigh | Left Shank | Right Shank |
|---|---|---|---|---|---|
| Chest | — | 20-30° | 20-30° | 40-50° | 40-50° |
| Left Thigh | 20-30° | — | 0-5° | 10-20° | 10-20° |
| Right Thigh | 20-30° | 0-5° | — | 10-20° | 10-20° |
| Left Shank | 40-50° | 10-20° | 10-20° | — | 0-5° |
| Right Shank | 40-50° | 10-20° | 10-20° | 0-5° | — |

TABLE 4

The possible signal (positive or negative) of the difference between first directions of each tracker placed on each specific part of the body. The signals presented regard the angles of arrival on the vertical plane (vertical plane is a parallel plane to the sagittal plane). The angle is considered as positive when at higher height of the virtual 0 axis on the vertical plane (perpendicular line to the coronal plane and parallel to the transverse plane on the computing device).

| Signal value Rel AoA – Z (vertical plane) | Chest | Left Thigh | Right Thigh | Left Shank | Right Shank |
|---|---|---|---|---|---|
| Chest | — | – | – | – | – |
| Left Thigh | + | — | +– near 0 | – | – |
| Right Thigh | + | +– near 0 | — | – | – |
| Left Shank | + | + | + | — | +– near 0 |
| Right Shank | + | + | + | +– near 0 | — |

Figure 6:
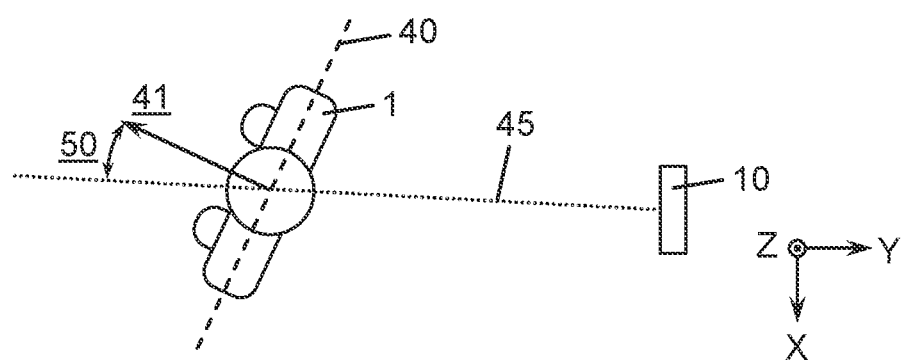
FIG. 6 diagrammatically shows a coronal plane of a user of a motion tracking system.

FIG. 6 diagrammatically shows a coronal plane 40 of a user of a motion tracking system.

The person 1 using the motion tracking system, i.e. the user, is substantially facing away from the computing device 10. Even in such situation, the computing device 10 is capable of assessing the positions of the trackers (not illustrated) even if they are arranged on a front-most part of the person 1 like in FIG. 4. The coronal plane 40 goes through the middle of the body of the person 1 and contains the head of the person 1; it will be noted that the dashed line of the coronal plane 40 illustrated a cross-section since it extends along the Z axis.

In some embodiments, the computing device 10 or each of the trackers 20a-20n receives data packets based on which the first direction (by performing the angle of arrival or angle of departure computations explained above) while the person is in such posture that a normal vector 41 of the coronal plane 40 forms an angle with a line 45 intersecting both the computing device 10 and a belly button of the person 1 having an absolute value less than or equal to 45°, like in FIG. 6.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the disclosure as defined in the claims.

The invention claimed is:

1. A motion tracking system comprising:
   (1) a plurality of trackers adapted to be arranged on a plurality of body members of a body of a person, each tracker comprising at least one inertial sensor and a plurality of tracker antennas arranged in an array, wherein each tracker of the plurality of trackers is configured to:
   receive, from a computing device, one or more first data packets through each of at least a first tracker antenna and a second tracker antenna of the plurality of tracker antennas of each of a first tracker and a second tracker of the plurality of trackers, the first tracker antenna and the second tracker antenna being set apart by a distance, and
   determine a first direction in which the computing device is relative to at least the first tracker and the second tracker by computing an angle of arrival of the one or more first data packets based on (i) a time of arrival of the one or more first data packets through each of the first tracker antenna and the second tracker antenna of the first and second tracker and (ii) a distance between the first tracker antenna and the second tracker antenna of the plurality of tracker antennas; and
   (2) the computing device, wherein the computing device is configured to:
   receive, from each tracker of the first tracker and second tracker, one or more second data packets comprising data indicative of the first direction of the first tracker and the second tracker,
   determine, based on the data included in the one or more second data packets received from each tracker of the plurality of trackers, a second direction in which each tracker of the plurality of trackers is relative to one or more other trackers of the plurality of trackers,
   determine, based on the first direction and the second direction determined for at least the first tracker and the second tracker, that positioning of at least the first tracker on a body member, of the plurality of body members, does not accord with a predetermined correspondence, the predetermined correspondence defining at least a first correspondence between the first tracker and a first body member of the plurality of body members and a second correspondence between the second tracker and a second body member of the plurality of body members,
   identify, based on the determining that the positioning of at least the first tracker on the body member does not accord with the predetermined correspondence, that at least the first tracker is misplaced on the body of the person, and
   modify at least one of the predetermined correspondence or an actual position of at least the first tracker based on the determining that the positioning of at least the first tracker on the body member does not accord with the predetermined correspondence and the identifying that at least the first tracker is misplaced on the body of the person.

2. The motion tracking system of claim 1, wherein the computing device is further configured to:
   receive, from each tracker of the plurality of trackers, at least one data packet comprising one or more measurements of the respective at least one inertial sensor at least while the tracker is arranged on the person; and
   provide a motion tracking sequence for the plurality of body members of the person based on both the received one or more measurements from each tracker of the plurality of trackers and the predetermined correspondence.

3. The motion tracking system of claim 1, wherein the plurality of tracker antennas comprise at least three antennas, arranged such that no three tracker antennas are arranged along a single line.

4. The motion tracking system of claim 1, wherein each second direction at least includes two perpendicular components thereby being at least indicative of a two-dimensional direction.

5. The motion tracking system of claim 1, wherein:
   the computing device is further configured to estimate a distance that the computing device is apart from each tracker of the plurality of trackers based on the second data packets received from each tracker of the plurality of trackers; and
   each second direction at least includes three perpendicular components thereby being indicative of a three-dimensional direction.

6. The motion tracking system of claim 5, wherein the determination that the positioning of at least the first tracker does not accord with the predetermined correspondence further comprises determining an actual position of each tracker on a surface of the respective body member on which the tracker is positioned relative to a predetermined position of the set of body members whose motion is tracked.

7. The motion tracking system of claim 1, wherein at least the plurality of trackers is configured to receive the first data packets using a wireless communications protocol comprising receiving a radiofrequency signal comprising the first data packets.

8. A motion tracking system comprising:
   a computing device configured to:
   receive, from at least a first tracker antenna and a second tracker antenna of a plurality of tracker antennas, the first tracker antenna and the second tracker antenna being set apart by a distance, one or more first data packets of a first tracker and a second tracker of a plurality of trackers at least while the first tracker and second tracker are positioned on a body of a person, wherein the plurality of trackers are adapted to be arranged on a plurality of body members of the body of the person, and each tracker comprising at least one inertial sensor and a plurality of tracker antennas arranged in an array;
   determine a first direction in which the computing device is relative to the first tracker and the second tracker by computing an angle of departure of the one or more first data packets based on (i) a time of arrival of the one or more first data packets from each of the first tracker antenna and the second tracker antenna and (ii) the distance between the first tracker antenna and the second tracker antenna of the plurality of tracker antennas of the respective tracker;
   determine, based on the first direction of the first tracker and the second tracker, a second direction in which the first tracker and the second tracker is relative to one or more other trackers of the plurality of trackers; and
   determine, based on the first direction and the second direction determined for at least the first tracker and the second tracker, that positioning of at least the first tracker on a body member, of the plurality of body members, does not correspond to accord with a predetermined correspondence, the predetermined correspondence defining at least a first correspondence between the first tracker and a first body member of the plurality of body members and a second correspondence between the second tracker and a second body member of the plurality of body members;

identify, based on the determining that the positioning of at least the first tracker on the body member does not accord with the predetermined correspondence, that at least the first tracker is misplaced on the body of the person; and modify at least one of the predetermined correspondence or an actual position of at least the first tracker based on the determining that the positioning of at least the first tracker on the body member does not accord with the predetermined correspondence and the identifying that at least the first tracker is misplaced on the body of the person.

9. The motion tracking system of claim 8, wherein the computing device is further configured to:

receive, from each tracker of the plurality of trackers, at least one data packet comprising one or more measurements of the respective at least one inertial sensor at least while the tracker is arranged on the person; and provide a motion tracking sequence of a plurality of body members of the person based on both the received one or more measurements from each tracker of the plurality of trackers and the predetermined correspondence.

10. The motion tracking system of claim 8, wherein the plurality of tracker antennas comprise at least three antennas, arranged such that no three tracker antennas are arranged along a single line.

11. The motion tracking system of claim 8, wherein each second direction at least includes two perpendicular components thereby being at least indicative of a two-dimensional direction.

12. The motion tracking system of claim 8, wherein the computing device is further configured to estimate a distance that the computing device is apart from each tracker of the plurality of trackers based on the second data packets received from each tracker of the plurality of trackers; and each second direction at least includes three perpendicular components thereby being indicative of a three-dimensional direction.

13. The motion tracking system of claim 12, wherein the determination that the positioning of at least the first tracker does not accord with the predetermined correspondence further comprises determining an actual position of each tracker on a surface of the respective body member on which the tracker is positioned relative to a predetermined position of the set of body members whose motion is tracked.

14. The motion tracking system of claim 8, wherein at least the computing device is configured to receive the second data packets using a wireless communications protocol comprising receiving a radiofrequency signal comprising the data packets.

15. A motion tracking system comprising:

a computing device comprising a plurality of computing device antennas, the computing device being configured to:

receive, from at least a first tracker antenna and a second tracker antenna of a plurality of tracker antennas of at least a first tracker and a second tracker of a plurality of trackers, each respective first tracker antenna and second tracker antenna being set apart by a distance, one or more first data packets through each antenna of the plurality of computing device antennas at least while the respective tracker is positioned on a body of a person, wherein the plurality of trackers are adapted to be arranged on a plurality of body members of the body of the person, and each tracker comprising at least one inertial sensor and a plurality of tracker antennas arranged in an array;

determine a first direction in which the computing device is relative to the first tracker and the second tracker of the plurality of trackers by computing an angle of arrival of the one or more first data packets based on (i) a time of arrival of the one or more first data packets at each antenna of the plurality of computing device antennas and (ii) the distance between the first tracker antenna and the second tracker antenna of the respective tracker;

determine, based on the first direction of the first tracker and the second tracker, a second direction in which the first tracker and the second tracker is relative to one or more other trackers of the plurality of trackers; and determine, based on the first direction and the second direction determined for at least the first tracker and the second tracker, that positioning of at least the first tracker on a body member, of the plurality of body members, does not accord with a predetermined correspondence, the predetermined correspondence defining at least a first correspondence between the first tracker and a first body member of the plurality of body members and a second correspondence between the second tracker and a second body member of the plurality of body members;

identify, based on the determining that the positioning of at least the first tracker on the body member does not accord with the predetermined correspondence, that at least the first tracker is misplaced on the body of the person; and modify at least one of the predetermined correspondence or an actual position of at least the first tracker based on the determining that the positioning of at least the first tracker on the body member does not accord with the predetermined correspondence and the identifying that at least the first tracker is misplaced on the body of the person.

16. The motion tracking system of claim 15, wherein the computing device is further configured to:

receive, from each tracker of the plurality of trackers, at least one data packet comprising one or more measurements of the respective at least one inertial sensor at least while the tracker is arranged on the person; and provide a motion tracking sequence of a plurality of body members of the person based on both the received one or more measurements from each tracker of the plurality of trackers and the predetermined correspondence.

17. The motion tracking system of claim 15, wherein the plurality of tracker antennas comprise at least three antennas, arranged such that no three tracker antennas are arranged along a single line.

18. The motion tracking system of claim 15, wherein:

the computing device is further configured to estimate a distance that the computing device is apart from each tracker of the plurality of trackers based on the second data packets received from each tracker of the plurality of trackers; and each second direction at least includes three perpendicular components thereby being indicative of a three-dimensional direction.

19. The motion tracking system of claim 15, wherein the determination that the positioning of at least the first tracker does not accord with the predetermined correspondence further comprises determining an actual position of each tracker on a surface of the respective body member on which the tracker is positioned relative to a predetermined position of the set of body members whose motion is tracked.

20. The motion tracking system of claim 1, wherein the modifying of the actual position of at least the first tracker comprises commanding provision of one or more user perceptible signals indicative of guidance on how to reposition at least the first tracker.

* * * * *

UNITED STATES PATENT AND TRADEMARK OFFICE
CERTIFICATE OF CORRECTION

PATENT NO. : 12,105,177 B2
APPLICATION NO. : 17/366664
DATED : October 1, 2024
INVENTOR(S) : Alves et al.

Page 1 of 1

It is certified that error appears in the above-identified patent and that said Letters Patent is hereby corrected as shown below:

In the Claims

In Column 18, Line 64, in Claim 8, after "does not", delete "correspond to"

Signed and Sealed this
Seventh Day of October, 2025

John A. Squires
*Director of the United States Patent and Trademark Office*